United States Patent
Gora et al.

(10) Patent No.: US 11,304,596 B2
(45) Date of Patent: Apr. 19, 2022

(54) APPARATUS, DEVICE AND METHOD FOR CAPSULE MICROSCOPY

(71) Applicant: THE GENERAL HOSPITAL CORPORATION, Boston, MA (US)

(72) Inventors: Michalina Gora, Somerville, MA (US); Dongyun Kang, Somerville, MA (US); Norman S. Nishioka, Wayland, MA (US); Brett Eugene Bouma, Quincy, MA (US); Guillermo J. Tearney, Cambridge, MA (US); Robert Carruth, Arlington, MA (US); Kevin Gallagher, Winchester, MA (US); Jenny Sauk, Somerville, MA (US); Moon Gu Lee, Suwon-si (KR); Nima Tabatabaei, Cambridge, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/353,555

(22) Filed: Mar. 14, 2019

(65) Prior Publication Data
US 2019/0261840 A1   Aug. 29, 2019

Related U.S. Application Data

(62) Division of application No. 13/898,798, filed on May 21, 2013.

(60) Provisional application No. 61/649,546, filed on May 21, 2012, provisional application No. 61/684,908, (Continued)

(51) Int. Cl.
*A61B 1/04*   (2006.01)
*A61B 1/00*   (2006.01)
*A61B 1/06*   (2006.01)
*A61B 5/00*   (2006.01)

(52) U.S. Cl.
CPC ............ *A61B 1/041* (2013.01); *A61B 1/0002* (2013.01); *A61B 1/00016* (2013.01); *A61B 1/00032* (2013.01); *A61B 1/00156* (2013.01); *A61B 1/00165* (2013.01); *A61B 1/00172* (2013.01); *A61B 1/043* (2013.01); *A61B 1/06* (2013.01); *A61B 5/0062* (2013.01); *A61B 5/0084* (2013.01); *A61B 5/0066* (2013.01); *A61B 5/0068* (2013.01); *A61B 5/0075* (2013.01)

(58) Field of Classification Search
None
See application file for complete search history.

(56) References Cited

U.S. PATENT DOCUMENTS

2007/0282403 A1 * 12/2007 Tearney ............... A61B 18/24 607/89
2007/0299309 A1   12/2007 Seibel
(Continued)

*Primary Examiner* — Amelie R Davis
*Assistant Examiner* — Marjan Saboktakin
(74) *Attorney, Agent, or Firm* — Quarles & Brady LLP

(57) ABSTRACT

An exemplary apparatus for obtaining data for at least one portion within at least one luminal or hollow sample can be provided. For example, the apparatus can include a first optical arrangement configured to transceive at least one electromagnetic radiation to and from the portion(s). The apparatus can also include a wavelength dispersive second arrangement, which can be configured to disperse the electromagnetic radiation(s). A housing can be provided with a shape of a pill, and enclosing the first and second arrangements.

22 Claims, 14 Drawing Sheets

Related U.S. Application Data filed on Aug. 20, 2012, provisional application No. 61/785,026, filed on Mar. 14, 2013.

(56) References Cited

U.S. PATENT DOCUMENTS

| | | | |
|---|---|---|---|
| 2008/0021275 A1* | 1/2008 | Tearney | A61B 5/0084 600/115 |
| 2008/0023012 A1 | 1/2008 | Dineen | |
| 2010/0268025 A1* | 10/2010 | Belson | A61B 1/041 600/109 |
| 2011/0208011 A1 | 8/2011 | Ben-Horin | |
| 2012/0004506 A1* | 1/2012 | Tearney | A61B 1/0008 600/116 |
| 2013/0013031 A1* | 1/2013 | Ben-Yehuda | A61B 5/073 607/92 |

* cited by examiner

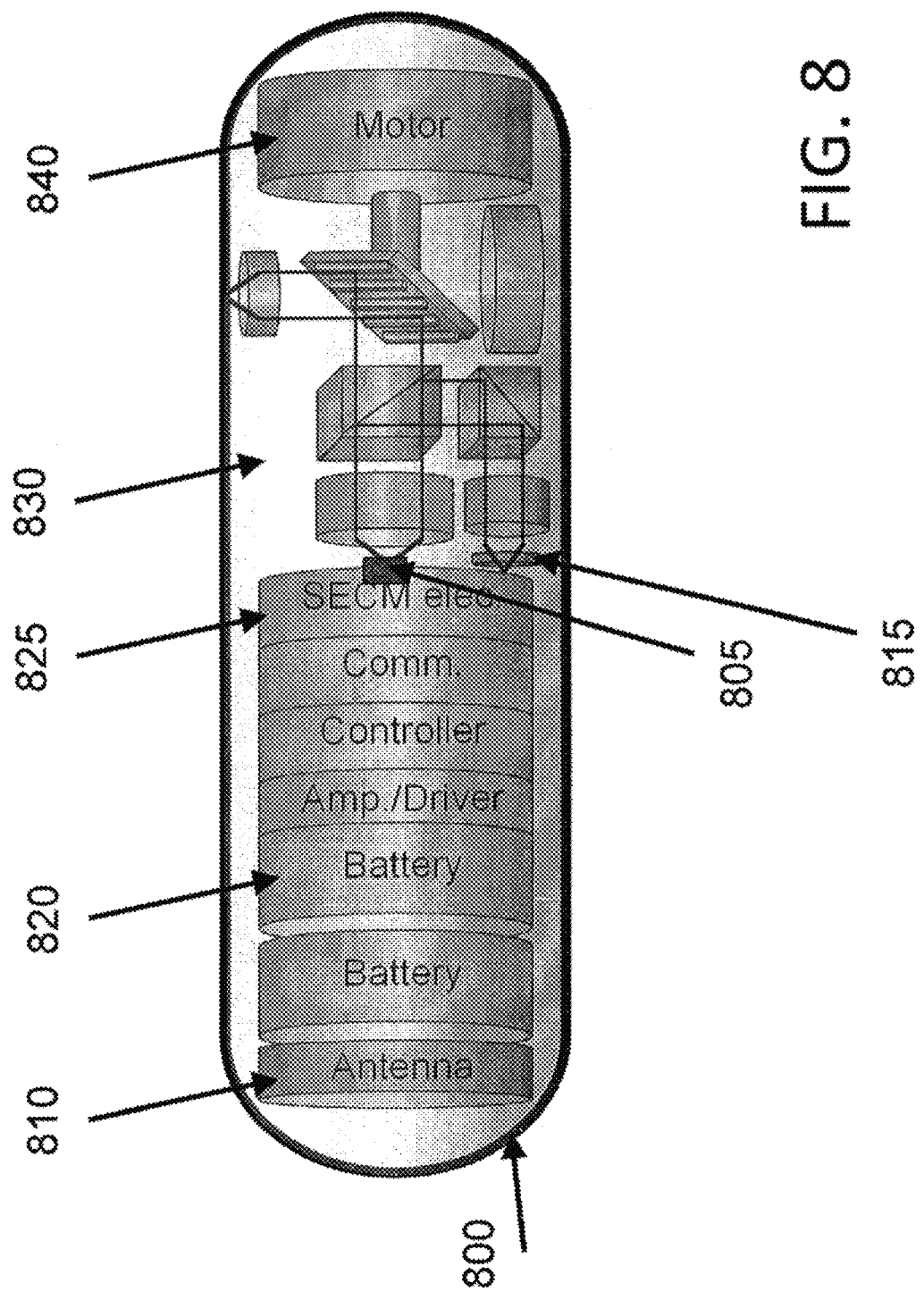

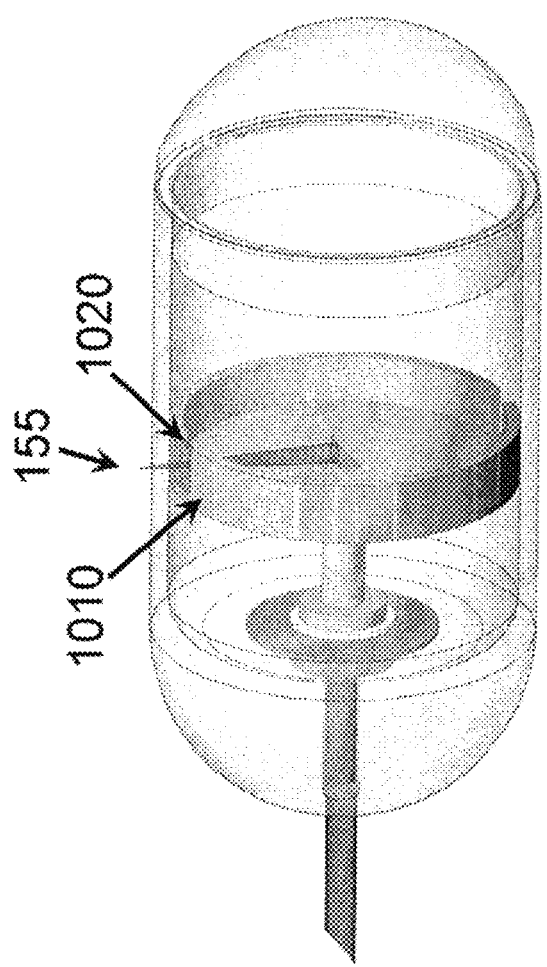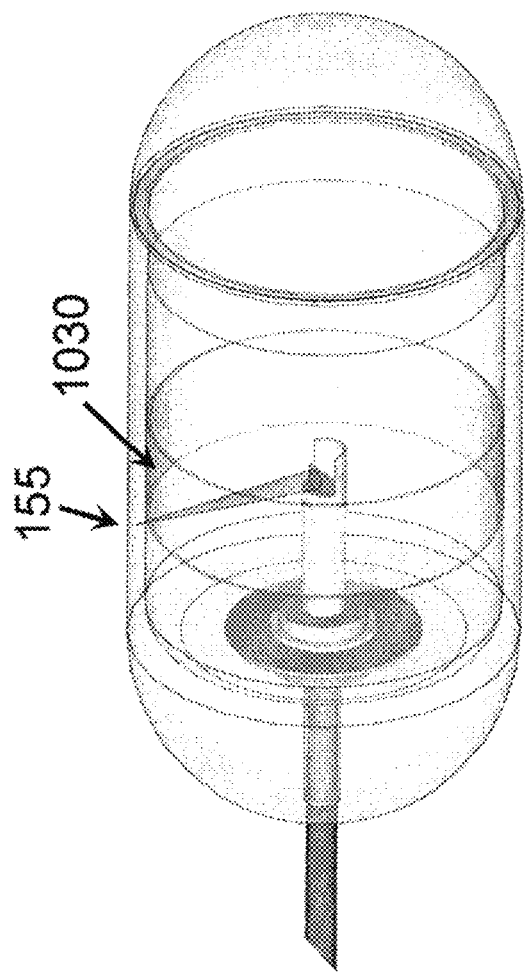

APPARATUS, DEVICE AND METHOD FOR CAPSULE MICROSCOPY

CROSS-REFERENCE TO RELATED APPLICATION(S)

This application is a divisional of U.S. patent application Ser. No. 13/898,798, filed May 21, 2013, which is based on, and claims the benefit of U.S. Provisional Patent Application No. 61/649,546, filed May 21, 2012, U.S. Provisional Patent Application No. 61/684,908, filed Aug. 20, 2012, and U.S. Provisional Patent Application Ser. No. 61/785,026, filed Mar. 14, 2013. Each of the foregoing applications is hereby incorporated herein by reference in its entirety for all purposes.

STATEMENT REGARDING FEDERALLY SPONSORED RESEARCH

This invention was made with government support under CA103769 awarded by the National Institutes of Health. The government has certain rights in the invention.

FIELD OF THE DISCLOSURE

Exemplary embodiments of the present disclosure relate to apparatus, device and method for imaging at least one portion of a structure, which is provided at or in one or more luminal organs, and more particularly to apparatus, device and method of capsule microscopy.

BACKGROUND INFORMATION

As is known in the art, introduction of endoscopy (esophagogastroduodenoscopy—"EGD") for visualization of digestive or gastrointestinal (GI) tract up to duodenum significantly has improved health care outcomes over a long period of time. This technique generally utilizes a flexible video-imaging probe, which can be advanced through a natural orifice to the luminal digestive organs. This procedure is considered to be minimally invasive. However, due to patients' discomfort, it is often performed under sedation. Sedation is one of the most important contributors to the high cost of upper endoscopy and is estimated to account for 30-50% of the total procedural cost. Because of the mortality and morbidity associated with complications related to sedation, patients likely undergo continuous cardiopulmonary monitoring and nursing support during the endoscopic procedure. Post-procedural recovery can also contribute to the expense, as it likely requires additional nursing and monitoring in a large and specialized physical space. After discharge, patients frequently need to be escorted home, and likely lose at least a day of work.

Besides cost, another limitation of upper endoscopy can be its relatively low accuracy. Studies have shown that endoscopists correctly identify the precancerous esophageal condition termed specialized intestinal metaplasia (SIM), in only approximately 40-50% of cases. Thus, for diagnostic purposes the gastroenterologist has to extract a tissue biopsy from several areas in the suspect region. The biopsy can then be processed and reviewed under a microscope by a pathologist who renders the final diagnosis. It is estimated that over 20 million such biopsies are excised and analyzed every year in the United States. Unfortunately, a biopsy represents only a fractional area of tissue, thus it can easily miss focal microscopic changes.

To address a need for a less invasive method for visualization of GI tract—capsule endoscopy (CE)—has been implemented. Since such time, a number of commercial products became available (e.g., Given PillCam and Intro-Medic MiroCam) in common use at GI clinics. Capsule endoscopy generally incorporates a miniaturized version of the camera and a radio transmitter. The unsedated subject swallows the capsule endoscope, which captures images of the GI tract, and transmits them remotely as it passes through the digestive system. This technique had a high impact on examination of the small intestine—area that usually cannot be seen by other types of endoscopy, such as EGD or colonoscopy. Conventional capsule endoscopy has been also used to evaluate Barrett's esophagus. Unfortunately, such conventional capsule microscopy usually suffers from a lack of control of the capsule at the GEJ, likely resulting in few viable images obtained at the critical region of the esophagus. Relatively poor diagnostic accuracy and the fact that the capsules are not reusable (e.g., a cost of one capsule can be about $450) capsule endoscopy have limited its benefit for Barrett's screening over conventional endoscopy. Recently, string capsule endoscopy (SCE) has been described, in which the commercially available capsule can be tethered with a string to facilitate a strict control of the pill camera's location, and a repeated visualization of the GEJ. SCE capsules may also be retrieved, sterilized, and reused, thereby likely significantly decreasing the cost of the capsule endoscopy. However, SCE can be subject to the same diagnostic accuracy limitations as endoscopy.

To improve diagnostic accuracy, a further class of imaging technologies providing an "optical biopsy" in living patients without excising any tissue, has been provided.

One such technology is a confocal laser endomicroscopy ("CLE"), based on tissue illumination with a low-power laser with subsequent detection through a pinhole of the fluorescence light reflected from the tissue. This technique has an improved spatial resolution, although it likely suffers from a very narrow field of view and also requires contrast agent in order to keep high quality of data. Clinical studies have shown that CLE can be a promising approach for an early detection of cancer in the GI tract. However, this procedure can be performed either with a dedicated endoscope or a probe that can pass through the accessory channel of a standard endoscope, which usually requires patient sedation. Another technique capable of "optical biopsy" is optical coherence tomography ("OCT") and its further modified form—termed optical frequency domain imaging ("OFDI").

In both such techniques, the tissue can be illuminated with near-infrared light, which can be detected after being back-scattered at the refractive index mismatch of cellular and sub-cellular components, providing images of tissue microstructure in vivo. The volumetric reconstruction of large sections of luminal organs can be achieved by the helical pullback scanning of the imaging optics. Based on clinical studies, this technique can provide structural cross-sections from entire lower esophagus, allowing for a BE diagnosis. Unfortunately, as in case of CLE, currently available OCT/OFDI catheters can be introduced during an endoscopy procedure, which usually requires sedation. Other techniques for optical biopsy can also be utilized, including confocal microscopy, spectrally-encoded confocal microscopy, and multi-photon and multi-harmonic microscopy. As with OFDI, these techniques also currently require sedated endoscopy for their implementation.

Accordingly, there may be a need to address at least some of the above-described deficiencies.

One of the areas for development in imaging of upper GI tract can include an improvement in diagnostic accuracy and decreasing cost of the procedure.

It is one of the objects of the present disclosure to provide apparatus, device and methods for obtaining microscopic image data from the GI tract that can be safe, highly tolerable to patients, and inexpensive. Such a device can be utilized, e.g., to screen a much larger population for GI tract diseases.

SUMMARY OF EXEMPLARY EMBODIMENTS

According to exemplary embodiments of the present disclosure, In accordance with the present invention, apparatus, device and method can be provided which can facilitate imaging of biological tissues, e.g., luminal organs in vivo, using optical techniques. The exemplary apparatus, device and method can utilize a tethered capsule catheter, which can facilitate delivery and collection of the light (e.g., and other electro-magnetic radiation(s)) illuminating a sample under review.

In one exemplary embodiment of the present disclosure, the tethered capsule catheter can comprise a swallowable rigid capsule connected to the distal end of a long, small diameter protective tether. The capsule can be made from, e.g., biomedical grade material and/or can have a diameter of about, e.g., 12.8 mm and a length of, e.g., about 24.8 mm, which can provide a comparable ratio to those of FDA-approved, commercially available capsule endoscopes (e.g., Givens G2, OMOM Capsule Endoscope). For imaging purposes, e.g., the capsule can comprise an imaging window, characterized with a high optical transparency. The window can be either on the side or the tip of the capsule for imaging of the luminal organs.

According to an exemplary embodiment of the present disclosure, when the capsule is swallowed, a person performing the procedure can use the tether for navigating the capsule within the upper gastrointestinal tract. The tether can be made of a clinical grade material, and can host inside an optical fiber. For example, the fiber can be placed inside of a driveshaft, if rotation of an optical fiber is preferable. At the distal end of the fiber, exemplary optics can be assembled, focusing the electro-magnetic radiation (e.g., light) transmitted through the fiber beyond the outer surface of the capsule. In one exemplary embodiment of the present disclosure, the optical fiber can be tapered or lensed to increase the numerical aperture of the fiber. In yet another exemplary embodiment of the present disclosure, a double clad or multi-clad fiber can be utilized.

In order to perform capsule endomicroscopy, the tethered capsule catheter can be optically coupled to designated imaging system. It can be used with microscopy system for microscopic two- and three-dimensional imaging. In that case a volumetric imaging in the capsule can be for example obtained by spinning of the optical probe inside the capsule and tether.

According to another exemplary embodiment of the present disclosure, an OFDI pill can be utilized. When such exemplary OFDI pill (including a capsule) is swallowed, the luminal organs constrict generally around the microscopy pill, and gradually push it down the gastrointestinal tract under the natural propulsion force of peristalsis. During its transit, multiple cross-sectional microscopic images can be acquired, stored and displayed in real-time. After the capsule reaches the distal most region of interest, it can be pulled back up through the esophagus to the mouth using, e.g., its tether. The gastroenterologist performing the procedure can control the capsule position during the procedure. The exemplary capsule can be sterilized and reused. In a study of 6 subjects, it was found that the mean transit time for a 20 cm length of esophagus was 52+/−20 seconds; the entire procedure lasted less than about 6 minutes from capsule insertion to extraction.

In one exemplary embodiment of the present disclosure, a tethered capsule endomicroscopy system/arrangement/apparatus can be provided, that can be utilizes by swallowing an optomechanically-engineered pill that captures cross-sectional, e.g., about 30 μm (lateral)×7 μm (axial) resolution, microscopic images of a gut wall, as it travels through the ldigestive tract. This exemplary technique can rapidly provide three-dimensional, microstructural images of the upper gastrointestinal tract in a simple and painless procedure, opening up new opportunities for screening for internal diseases.

Accordingly, an exemplary apparatus for obtaining data for at least one portion within at least one luminal or hollow sample according to an exemplary embodiment of the present disclosure can be provided. For example, the exemplary apparatus can include a first optical arrangement configured to transceive at least one electromagnetic radiation to and from the portion(s). The apparatus can also include a wavelength dispersive second arrangement which is configured to disperse the electromagnetic radiation(s). A housing can be provided with a shape of a pill, and enclosing the first and second arrangements.

A tether arrangement can be provided that is connected to the outer periphery. The apparatus can also include a further arrangement that is configured to track at least one of position, acceleration or velocity of the tether and/or of the apparatus. A video camera arrangement can also be connected to the outer periphery.

In a further exemplary embodiment of the present disclosure, another apparatus for obtaining data for at least one portion within at least one luminal or hollow sample can be provided. Such exemplary apparatus can include an optical first arrangement configured to transceive at least one electromagnetic radiation to and from the portion(s). A second arrangement can be provided which is configured to forward at least one return radiation from the luminal or hollow sample(s) to an optical microscopy system, whereas at least one portion of an outer periphery of the apparatus has a shape of a pill. A tether arrangement can be connected to the outer periphery.

For example, the tether can contain an optical fiber drive shaft. An imaging arrangement can be provided which can generate an image when the optical fiber drive shaft rotates and causes the electromagnetic radiation(s) to generate a particular pattern on the luminal or hollow sample(s). The tether and the pill can travel along the luminal or hollow sample(s) so as to generate a further pattern, and the luminal or hollow sample(s) can generate the image based on the particular pattern and the further pattern. A further arrangement can be provided that is configured to track information, which is position, acceleration and/or velocity of the tether. An imaging arrangement can be provided which can generate and correct an image of the luminal or hollow sample(s) based on the information. Another arrangement can be coupled to the tether, which can facilitate a grasping of the tether without compressing the tether.

According to a further exemplary embodiment of the present disclosure, yet another arrangement can be provided which is configured to provide a further radiation to the luminal or hollow sample(s), which can cause a change thereto. A motor arrangement can be provided which is configured to rotate at least a portion of the first arrangement. A video camera arrangement can be provided which is connected to the tether, and an imaging third arrangement can be provided which can generate a further image of the at least one luminal or hollow sample based on OCT, SECM, OFDI, confocal, 2 photon, 3 photon, fluorescence, and/or Raman modality. The first arrangement can comprise a ball lens, and a further arrangement can be provided around the tether, and configured to prevent damage of the when the tether is impacted. A third arrangement can be provided which is configured to disperse the electromagnetic radiation(s).

A further exemplary apparatus for obtaining data from at least one portion within at least one luminal or hollow sample according to still another exemplary embodiment of the present disclosure can be provided. Such further apparatus can include a first optical arrangement configured to transceive at least one electromagnetic radiation to and from the portion(s). The apparatus can also include a second arrangement which is configured to forward at least one return radiation from the luminal or hollow sample(s) to a non-interferometric optical microscopy system, whereas at least one portion of an outer periphery of the apparatus can have a shape of a pill.

According to a still further exemplary embodiment of the present disclosure, a third arrangement can be provided which can includes (i) a battery arrangement which provides energy to the optical microscopy system, (ii) a radio frequency transmitter arrangement, (ii) a light source arrangement, and/or (iv) a data storage arrangement. A propulsion arrangement can also be provided which moves the apparatus within the at least one luminal or hollow sample. These and other objects, features and advantages of the present disclosure will become apparent upon reading the following detailed description of exemplary embodiments of the present disclosure, when taken in conjunction with the appended drawings, and the claims, which follow.

BRIEF DESCRIPTION OF THE DRAWINGS

Further objects, features and advantages of the present disclosure will become apparent from the following detailed description taken in conjunction with the accompanying drawings showing illustrative embodiments of the present invention, in which:

FIG. 8 is an exemplary embodiment of a wireless SECM capsule according to an exemplary embodiment of the present disclosure;

FIG. 10A is perspective view of a common path OCT capsule with reference arm reflective surface mounted together with the optical probe according to an exemplary embodiment of the present disclosure;

FIG. 10B is perspective view of another common path OCT capsule with the reference arm reflective surface mounted on the capsule wall according to a further exemplary embodiment of the present disclosure;

FIG. 11, panel (b) is a close-up, time-integrated photograph of the exemplary tethered capsule endomicroscope device of FIG. 11, panel (a), transmitting red light as the internal optics rotate;

FIG. 11, panel (c) is another photograph of the exemplary tethered capsule endomicroscope device, in which the tether (arrow) is very flexible and a plastic ball, attached to the tether (arrowhead), facilitates manipulation of the device;

FIG. 11, panel (d) is an exemplary tethered capsule endomicroscopy image of a normal esophagus, obtained from a normal volunteer in vivo, which utilizes the exemplary tethered capsule endomicroscope device shown in FIG. 11, panel (a);

FIG. 11, panel (e) is an expanded view of the image shown in FIG. 11, panel (d) which demonstrates the normal esophageal wall architectural morphology, including the squamous epithelium (E), muscularis mucosa (MM), lamina propria (L), submucosa (S), containing blood vessels (arrowheads), inner and outer muscularis (IM) and (OM), and myenteric plexus (MP);

FIG. 11, panel (f) is an exemplary tethered capsule endomicroscopy cross-sectional image of the stomach, obtained from a normal volunteer in vivo, which utilizes the exemplary tethered-capsule endomicroscope device shown in FIG. 11, panel (a);

FIG. 11, panel (g) is expanded view of the exemplary image of FIG. 11, panel (f) displaying characteristic glandular "pits" (arrowheads);

FIG. 11, panel (h) in an exemplary image obtained from a patient with histopathologically-confirmed Barrett's esophagus in vivo, which utilizes the exemplary tethered capsule endomicroscope device shown in FIG. 11, panel (a);

FIG. 11, panel (i) is expanded view of the exemplary image of FIG. 11, panel (h) illustrating an irregular luminal surface, heterogeneous backscattering and glands within the mucosa (arrowheads);

FIG. 12, panel (b) is a portion of a cross-sectional tethered capsule microscopy image from a patient with a diagnosis of Barrett's esophagus with architectural atypia suggestive of high-grade dysplasia that can be seen in the middle of the esophagus, which utilizes the exemplary tethered capsule endomicroscope device shown in FIG. 11, panel (a);

FIG. 12, panel (c) is a portion of a cross-sectional tethered capsule microscopy image, illustrating squamous mucosa that can be seen at the proximal end of the esophagus, which utilizes the exemplary tethered capsule endomicroscope device shown in FIG. 11, panel (a);

FIG. 12, panel (d) is a three-dimensional representation of the tethered capsule endomicroscopy dataset providing an exemplary 4 cm segment of Barrett's esophagus with multiple raised plaques/nodules, one of which corresponds to the features shown in FIG. 12, panel (b);

FIG. 12, panels (e)-(g) are exemplary three-dimensional flythrough views of the stomach, Barrett's segment, and squamous mucosa, respectively, which utilizes the exemplary tethered capsule endomicroscope device shown in FIG. 11, panel (a), demonstrating a difference between the superficial appearance of the rugal folds of the stomach, the crypt pattern of Barrett's esophagus, and the smooth surface of the squamous mucosa FIG. 13, panel (a) is an overview diagram of the tethered capsule endomicroscopy device, according to an exemplary embodiment of the present disclosure.

Figure 1:
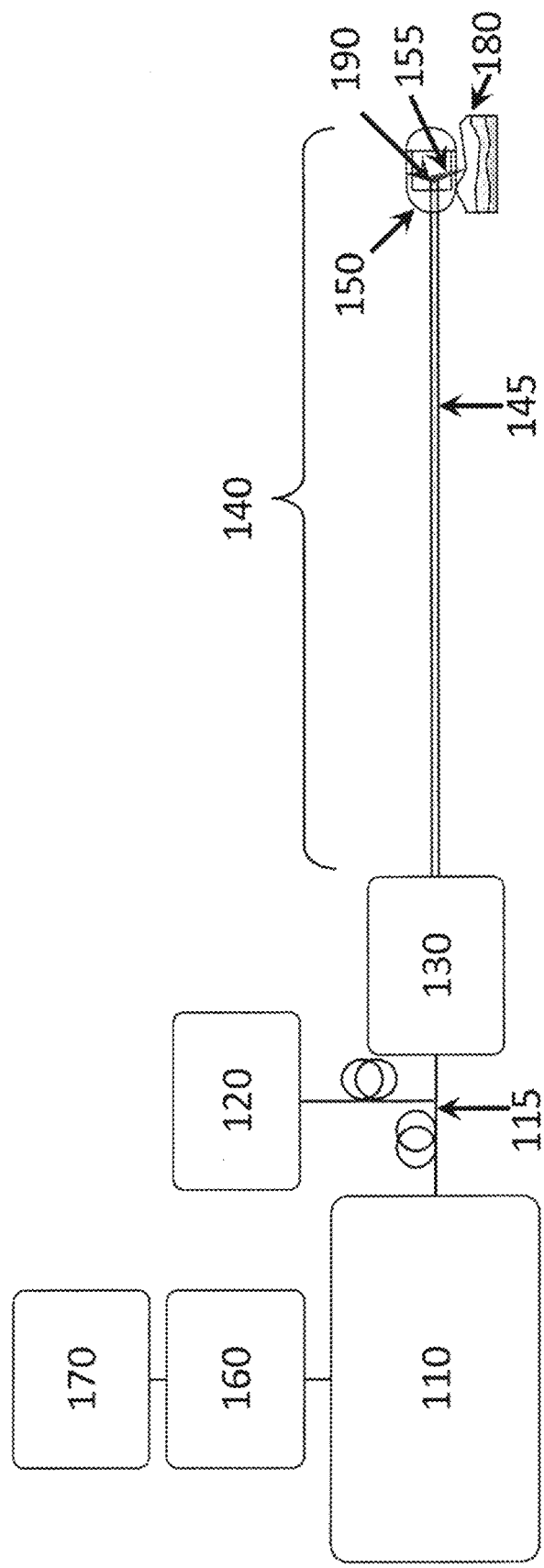
FIG. 1 is a block diagram of an imaging system according to an exemplary embodiment of the present disclosure which can include a capsule catheter.

Throughout the drawings, the same reference numerals and characters, if any and unless otherwise stated, are used to denote like features, elements, components, or portions of the illustrated embodiments. Moreover, while the subject disclosure will now be described in detail with reference to the drawings, it is done so in connection with the illustrative embodiments. It is intended that changes and modifications can be made to the described exemplary embodiments without departing from the true scope and spirit of the subject disclosure.

DETAILED DESCRIPTION OF EXEMPLARY EMBODIMENTS

FIG. 1 shows a block diagram of an optical imaging capsule catheter system/apparatus according to an exemplary embodiment of the present disclosure of. This exemplary apparatus can include a microstructural imaging system 110, an optical fiber 115, a high power laser source for guided biopsy, laser marking, or tissue treatment 120, an optical junction 130, an optical imaging catheter 140, a data acquisition, a processing and storage arrangement 160 and a data display arrangement 170. The microstructural imaging system 110 can utilize at least one of optical frequency domain imaging, optical coherence tomography, spectral domain OCT, confocal microscopy, spectrally-encoded confocal microscopy, two photon microscope, second harmonic microscopy, third harmonic microscope, CARS, stimulated Raman microscopy, etc. For example, such imaging system 110 can detect electro-magnetic radiation (e.g., remitted light) from a tissue 180 to acquire and/or determine information regarding microstructures on or in the tissue 180.

The optical signals from both microstructural imaging modality and marking/treatment laser platform can be coupled into the fiber 115 (e.g., single or multi mode) that can be connected to the optical junction 130. The optical junction 130 can serve as an interface between the stationary imaging systems and the stationary or rotating optical core 190 in the capsule catheter 140. The capsule catheter 140 can comprise a small diameter, flexible, soft, smooth and sleek tether 145, which—in one exemplary embodiment—can be configured to minimize stretching, terminated at the distal end with a capsule 150. A size of the capsule 150 can facilitate it to be swallowed. In one exemplary embodiment, the capsule 150 can have a diameter of less than about 2 cm and a length of less than about 4 cm. In yet another exemplary embodiment, the diameter of the capsule 150 can be less than about 1 cm.

The capsule catheter 140 can enclose an optical core 190, which can deliver and/or collect light 155 to and/or from the imaged tissue 180. Radiation (e.g., light) returning from the tissue 180 can be detected by the microstructural imaging system 110. The detected signal can be acquired by the data acquisition system 160, which also can be responsible for the data processing and storage. The data can be processed and/or displayed using the display arrangement 170 in a real-time, e.g., for a proper operation, and thereafter, for further visualization and analysis. In one exemplary embodiment, the data can be displayed using three-dimensional rendering. In another exemplary embodiment, the three-dimensional rendering can be made to be a more accurate representation of the anatomical structure by use of positional information that is obtained by tracking the location of the tethered sheath external to the body or by a position sensor arrangement contained within the tether or capsule itself.

Figure 2:
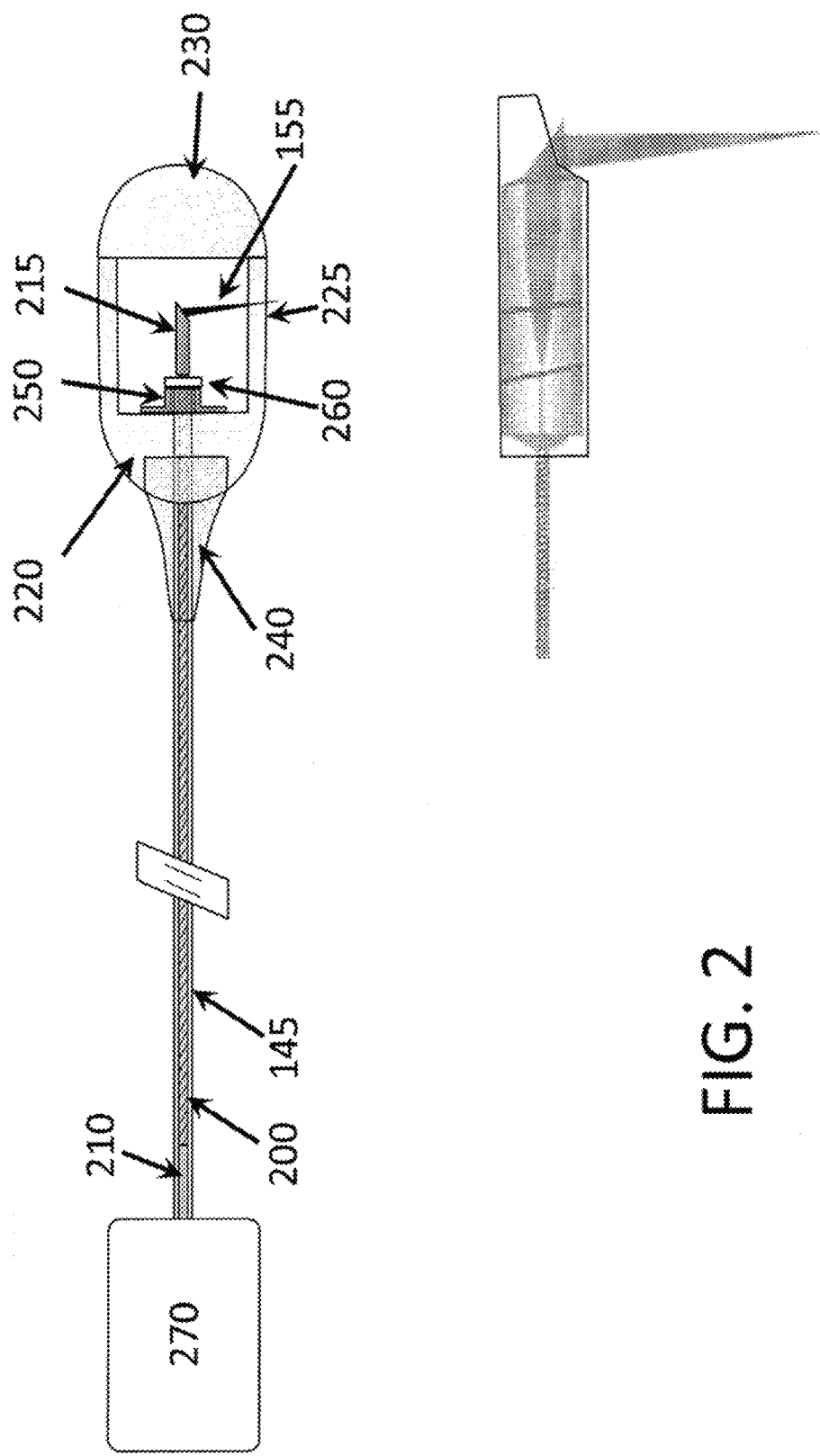
FIG. 2 is a schematic cross-sectional diagram of an exemplary embodiment of a capsule catheter according to the present disclosure having a spinning optical core arrangement.

FIG. 2 a schematic cross-sectional diagram of a capsule catheter with a spinning inner optical core according to an exemplary embodiment of the present disclosure. For example, the distal imaging portion of the optical core can be centered in the luminal organ using the capsule. The fiber delivering electro-magnetic radiation (e.g., light) to the capsule part can be protected by a static tether 145. In this exemplary embodiment, the capsule can comprise a proximal base 220 with an imaging window portion 225 and a distal cap 230. It can be beneficial to provide the capsule that is divided into at least two parts during catheter assembling process. After the assembly, the distal cap 230 can be attached to the proximal base 220 such that the capsule is sealed. Such seal can be facilitated, for example, by permanent epoxying or using a snap connection at cap with O-ring to facilitate non-permanent seal, if required or beneficial.

The capsule can be made of rigid or soft material. In one exemplary embodiment, a PMMA, polycarbonate or other material, which is a clear, easily polished, rigid, strong, medical grade and easily bonding can be used. As shown in FIG. 2, an exemplary spherocylindrical shape of the capsule is illustrated, with an exemplary size of about 12.8 mm diameter and about 24.8 mm in length. The capsule shape can be provided in a way to engage peristalsis, and also to facilitate easy swallowing and retracting, e.g., tear drop shape. In addition, different sizes for the shape can be used depending on the patient height and BMI. To ease the swallowing procedure, the exemplary capsule can be dipped in a fluid, such as water or saline, or coated with special coatings lowering friction coefficient. The exemplary capsule can be also filled with liquids such as water or gases in order to improve imaging properties. According to another exemplary embodiments of the present disclosure, the outer surface of the capsule can contain a non-toxic coating designed to be dissolved upon swallowing, and that can impart a change in the tissue properties that provides additional contrast for imaging. In one such exemplary embodiment, the coating can include an acetic acid, an acetic acid derivative and/or an acidic compound that increases contrast of the nuclei of cells.

According to the exemplary embodiment shown in FIG. 2, a part of the capsule used for imaging—an imaging window 225—can be side-facing, situated in the center of the capsule. The imaging window 225 can be also situated at the distal cap 230 of the capsule if forward facing is utilized. The imaging window 225 can be transparent for the light used for imaging, and its thickness can be design to decrease its influence on the imaging properties. Such exemplary imaging window 225 can be coated with antireflective film, tilted or drafted or wedged to reduce backreflection. Additional marks or irregularities can be added in the region of the imaging window 225 for data processing and/or orientation in the esophagus during the procedure.

The proximal capsule base 220 shown in FIG. 2 can have an opening to facilitate an assembly with the tether 145, and keep an open lumen for spinning the inner optical core. The base 220 material can be partially transparent to facilitate easier assembly and quality assurance to ensure proper epoxy bonding. The fixation of the tether 145 to the capsule can depend on the material of the tether 145. In order to facilitate maximum bonding, certain provisions can be utilized to match an approximate material elastic modulus of the tether 145 structural material to components of the capsule. In one exemplary embodiment, if the tether 145 comprises a metal shielding, a collar 250 made of brass or other material can be used for an improved bonding. In order to prevent the tether 145 from kinking close to its connection with the capsule, a strain relief tail 240 can be added. A shape of the tail 240 can match curves of the capsule or other element to facilitate a smooth transition. The tale 240 can be made of urethane, nylon and/or another medical grade, flexible, while relatively hard polymer and can be provisioned at the capsule base 220. The tale 240 can be also shaped from epoxy and/or other material. The tail 240 can be epoxied to the capsule base 220 and the tether 145. Flexible epoxies can be used at strain relief junction and rigid epoxies can be used at acrylic contacts.

In the exemplary embodiment shown in FIG. 2 the tether 145 can be a long, small diameter tube composed of a material, e.g., preventing the stretching of the tether 145, e.g. a stainless steel flat wire coil or wire weave, coated on the outside with polyethylene, polyimide or pebax to assure smoothness and tear resistance and on the inside coated with polyimide Teflon copolymer or teflon inner lining to assure low friction coefficient. The tether 145 can be water sealed and have single lumen or multilumen to facilitate filling/draining/ventilating of the capsule with liquid, gas or air. In one exemplary embodiment, the tether 145 can be similar to a steerable catheter facilitating a maneuverability of the capsule at the end of the tether 145. The inner surface of the tether 145 can be lined with Teflon or special coating to decrease friction coefficient, or the lumen can be filled with lubricant in order to allow uniform spinning of the optical core.

The optical core can comprise a long, small diameter driveshaft 200, which can be, e.g., Teflon coated for minimizing friction during rotation. The driveshaft 200 can deliver a torque of the enclosed optical fiber along the length of the catheter. The driveshaft 200 can be attached to the proximal optical connector 270 by proximal protective tube 210 (e.g., metal, plastic). The distal part of the optical probe can be enclosed in the distal tube 215 (e.g., metal, glass, plastic). According to one exemplary embodiment, the distal tube 215 can facilitate a linearity among optical components, fiber and driveshaft. Such distal tube 215 can extend past the optical probe 190 to protect it from a contact with a capsule. The distal tube 215 can have an opening either on the side or top to avoid blocking the light beam 155. In order to facilitate a uniform spinning of the optical probe, a base (e.g., proximal part) of the distal tube 215 should likely, e.g., not be in contact with any material, or, as provided in exemplary embodiment shown in FIG. 2, a Teflon washer 260 can be used. The Teflon washer 260 can be threaded over the driveshaft and separate the rotating distal tube 215 from the static collar 250.

Figure 3:
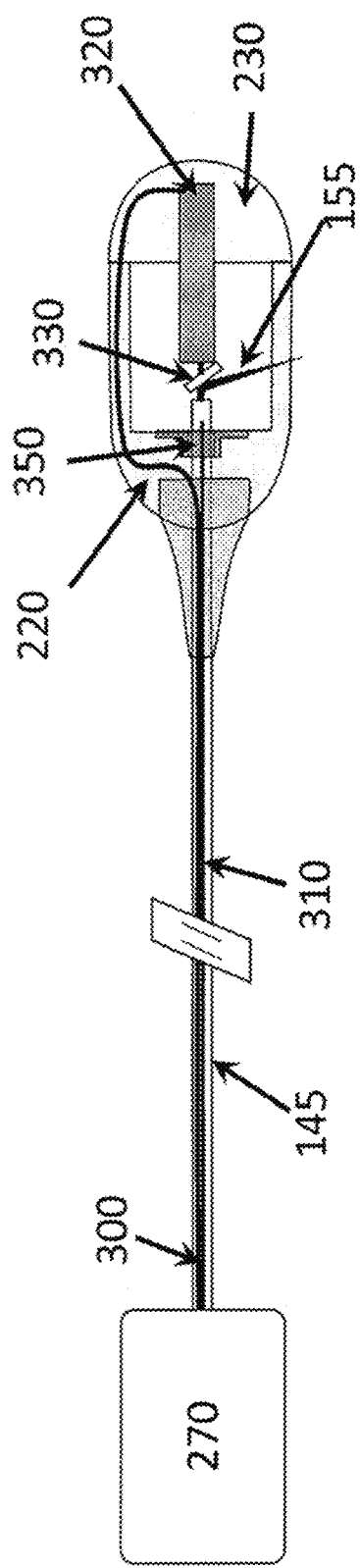
FIG. 3 is a schematic cross-sectional diagram of an exemplary embodiment of a capsule catheter of the present disclosure with a motor spinning distal optics arrangement.

FIG. 3 shows a schematic cross-sectional diagram of an exemplary embodiment of a capsule catheter according to the present disclosure with a motor spinning distal optics arrangement. In this exemplary embodiment, the optical probe can be static along a tether 145 and a capsule base 220. Rotating a reflective optical element 330, mounted on a small motor 320, can facilitate the spinning of the imaging beam 155. The motor 320 can be mounted off center, with possible provisions for belts or gear assemblies in a distal capsule cap 230 or in a proximal capsule base 220. The motor 320 can be mounted in the center of the distal capsule cap 230, or in the proximal capsule base 220 if a hollow core motor can be used. A collar 350, in such exemplary embodiment or according to any other exemplary embodiment, can be flipped in comparison to the collar 250 position as shown in FIG. 2, to obtain additional space in the capsule. A current can be delivered to the motor 320 and to an encoder via wires 300, for example, embedded in one or more of the lumens of the tether 145. In this exemplary embodiment, the tether 145 can have a strengthen lumen protecting a fiber in optical core. In another exemplary embodiment, the motor 320 can be powered using the batteries.

According to further exemplary embodiments, the optics arrangement can include a high numerical aperture objective lens, an aspheric lens, a ball lens, a GRIN lens, a diffractive optical element, and/or a diffraction grating to spectrally disperse different wavelengths along different spatial locations in the sample where the spatial locations differ along a dimension that is substantially parallel to the tissue surface. At least some of these optical elements can be attached to the spinning mechanism that includes at least one of a driveshaft or motor. Alternatively, such exemplary optics arrangement(s) can be translated using a translation means such as a translating driveshaft or a linear motor that resides within the capsule.

Figure 4:
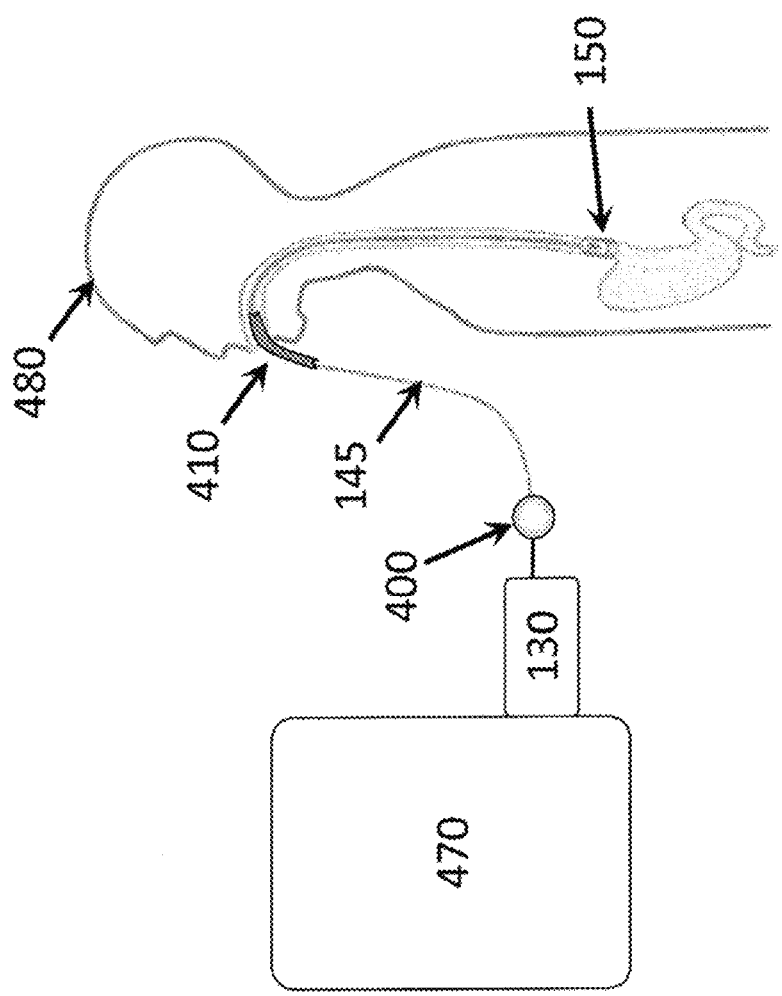
FIG. 4 is a diagram of an exemplary clinical realization of imaging procedure using the capsule catheter according to an exemplary embodiment of the present disclosure.

FIG. 4 shows a diagram of an exemplary clinical realization of imaging procedure using an exemplary capsule catheter according to an exemplary embodiment of the present disclosure. The capsule catheter can be sterilized in advanced, and connected to an optical junction 130 just before a procedure. A trained person performing the procedure can control the position of a capsule 150 using a ball handle 400 and a tether 145. The subject 480 does not need to be sedated during the procedure. The subject/patient 480 can sip water with a straw or from a cap to facilitate swallowing the capsule 150. Sips of water can assist in peristalsis of the capsule 150. Images can be obtained while the patient 480 is in various positions. The subject 480 can be asked to wear a pediatric bite block, mouth guard or a particularly designed tube 410 can be slid into the mouth after swallowing to prevent from biting of the tether 145. The distance from the mouth entrance to the swallowed capsule 150 can be established via, e.g., distance marks on the outer sheath of the tether 145.

Volumetric images of the esophagus can be obtained during descending of the capsule 150, with spinning the optical core or rotating the motor, through the esophagus into the stomach, providing helical scanning of light beam over the luminal organ. Additional arrangement(s) for obtaining the location of the capsule in the GI tract can be provided, including a video camera placed outside the mouth to track the location of the sheath with or without additional illumination, which can be coherent resulting in a speckle pattern formed on the sheath. In such an embodiment, the velocity of the sheath can be determined by cross-correlating the externally imaged speckle pattern remitted from the sheath. Additional position sensing procedures according to certain exemplary embodiments of the present disclosure can include and/or utilize position-sensing mechanisms internal to the catheter or fiber sensors embedded in the tether sheath.

The exemplary images can be processed and displayed by the imaging console 470 in real time, this facilitating an assessment of the current position in upper GI tract. For example, the time between the swallowing of the capsule and about 50 cm distance from the mouth can be recorded to assess the time used for peristalsis to assist the mobility of the capsule 150. Then, using the tether 145, the capsule 150 can be pulled back until a mild resistance is felt (e.g., the lower esophageal sphincter) and the subject can be asked to dry swallow or swallow water to open the lower esophageal sphincter. Meanwhile, the capsule 150 can be slowly pulled back up from the lower esophageal sphincter, and imaging can occur during the manual pullback.

One of the advantages of the tethered capsule design can be that the imaging procedure can be repeated to obtain appropriate distal esophageal images and/or to investigate interesting regions in a more accurate manner. It can be also used for keeping the capsule in a certain position for marking of treatment of the diseased tissue. After the exemplary procedure, the tether 445 can be pulled back until the capsule 450 is retrieved from the patient's mouth. In yet another exemplary embodiment, the sheath of the tether 145 can be pulled back automatically using a translation stage. In yet another exemplary embodiment, the internal driveshaft and optical core can be pulled back inside the sheath, while the sheath remains relatively stationary.

As shown in FIG. 4, a ball handle 400 or the tether 145 can be used by the operator for controlling of the capsule position and also can protect the capsule from passing the distance of about 60 cm in upper GI tract. In this exemplary embodiment, the ball of the ball handle 400 can be a 1" ball, which can be made of a biocompatible material. The shape of the ball handle 400 can be contoured to the hand for easy holding. In an exemplary embodiment, the handle 400 can be firmly bound to the tether 145, while not collapsing the inner lumen of the tether 145. In another exemplary embodiment, the ball handle 400 can be removed or translated along the tether 145 during advancing of the capsule 150. The ball handle 400 can include strain relief tails, e.g., to reduce the risk of the tether 145 kinking or shearing, similar to the tail 240 presented at FIG. 2. at the tether—capsule interface. The ball handle 400 can facilitate custom interchangeable hand attachments, designed specifically for the operator. The ball handle 400 can include a clicker or button, either wired or wireless, for example to facilitate the clinician to document notation points for easy later review, or to document points of interest, GE junction, 20 cm, 30 cm, etc.

Figure 5:
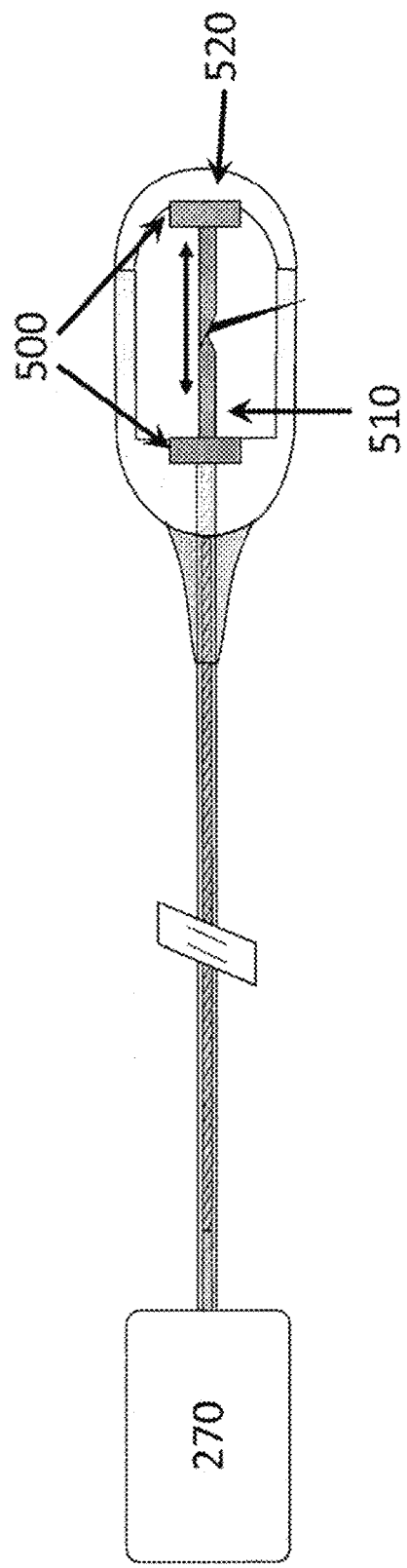
FIG. 5 is a schematic cross-sectional diagram of a capsule catheter with a short automatic pullback according to an exemplary embodiment of the present disclosure.

Exemplary embodiments shown in FIG. 2 and FIG. 3 facilitate images to be obtained from different lengths of the esophagus, either by peristalsis or manual pulling of the capsule. The process of pulling can be also automatic in order to keep the constant velocity and constant distance between consecutive circumferential frames, by using a motor pullback segment outside of the patient. In certain exemplary applications, such as, e.g., marking or treatment of the tissue, a short, fast and fully automatic pullback can be useful, as shown in the exemplary embodiment of FIG. 5. In this exemplary case, bearings or low friction collars 500 can reside in the proximal and/or distal cap. In combination with a specially designed probe housing 510, collars 500 can facilitate a smooth short pullback of the optical core. A probe housing 510 can be used as a bearing surface to provide a more linear motion, and centered wobble-minimized rotation. A telescopic function and spring can be used to integrate with a distal and proximal cap bearing surface, particularly beneficial for a scanning probe. In order to gain more space in the capsule, for this and/or any other exemplary embodiment, a distal cap 520 can be hollowed out with cavity to allow freer movement/extension of the optical core.

In one exemplary embodiment, a space of the distal cap 520 or other part of the capsule or distal end of the tether can be used for incorporating white light camera facilitating an acquisition of images from the surface of the esophagus. The capsule catheter can be also incorporated with additional elements for taking multiple biopsies, such as, e.g., a biopsy needle controlled by spring actuation, mechanical actuation, or piezoelectric actuation. In yet another embodiment, the cap of the capsule can extend and collapse, trapping tissue in the cap of the capsule. The capsule can be also used for monitoring of different processes in esophagus, e.g., motility with an integrated pressure sensor; temperature sensor to detect esophageal temperature while monitoring for any esophageal injury deep to the mucosal layer; marking capabilities to target areas of dysplasia in Barrett's esophagus or to identify areas of histologic significance such as areas of esophageal fibrosis in patients with eosinophilic esophagitis.

Figure 6:
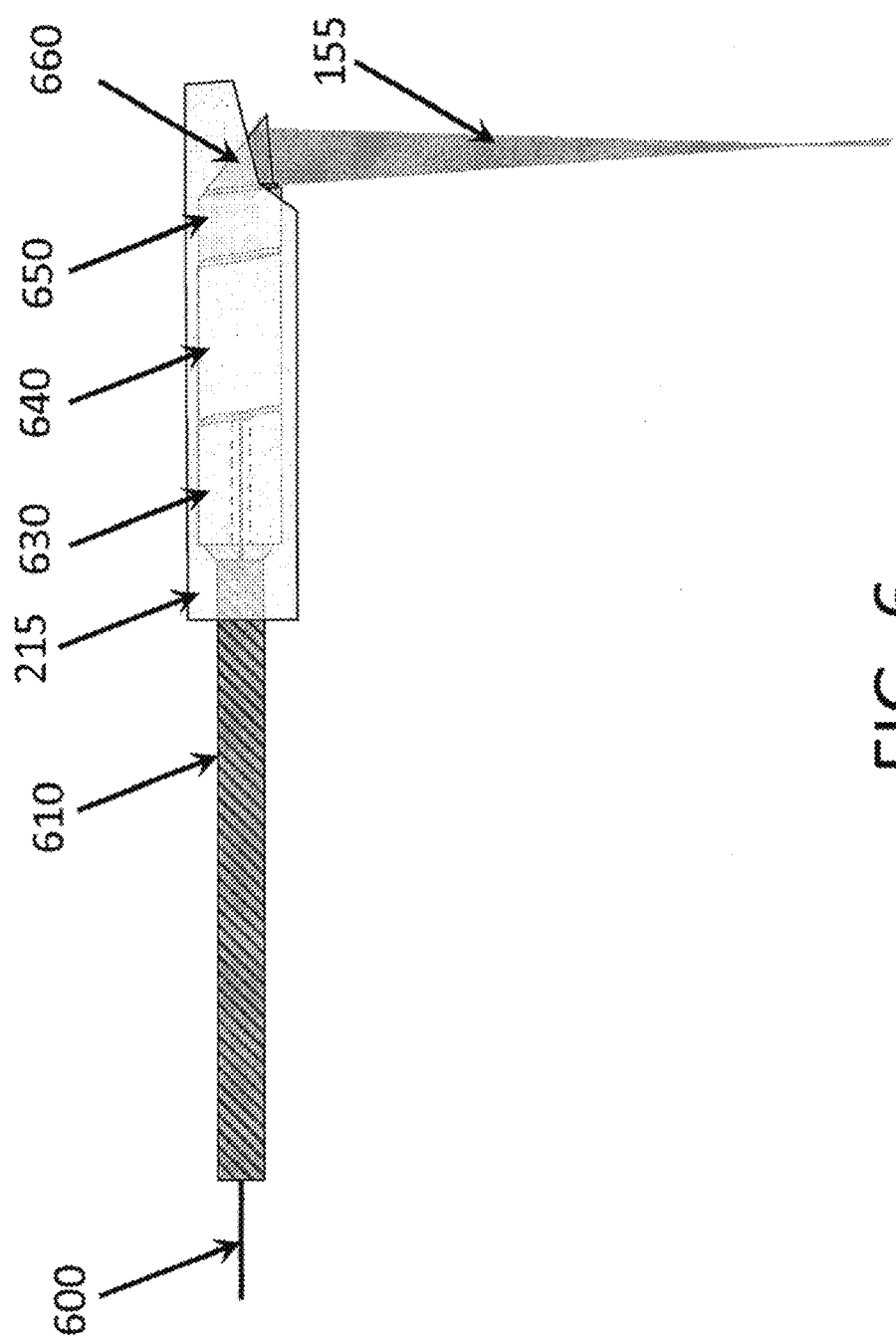
FIG. 6 is a schematic cross-sectional view of an exemplary optical system for focusing light beam at the tissue in the luminal organs imaging system according to an exemplary embodiment of the present disclosure.
Figure 9:
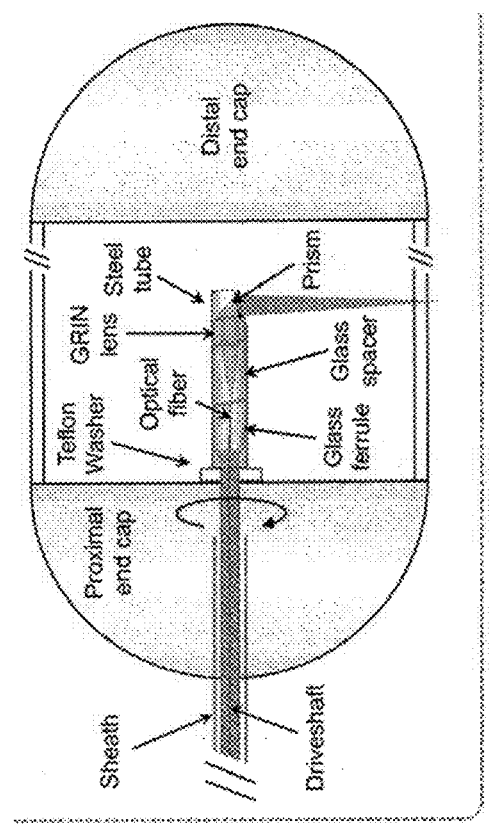
FIG. 9 is a schematic cross-sectional diagram of another exemplary embodiment of the capsule catheter according to the present disclosure also having a spinning optical core arrangement.
Figure 11B:
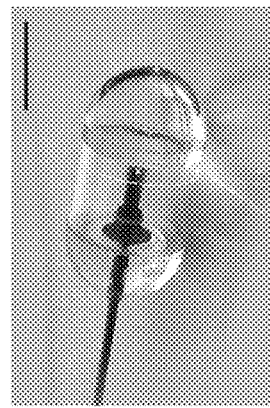
FIG. 11, panel (a) is a photograph of an exemplary tethered capsule endomicroscopy device, showing the capsule portion adjacent to a penny for scale, according to an exemplary embodiment of the present disclosure.
Figure 11C:
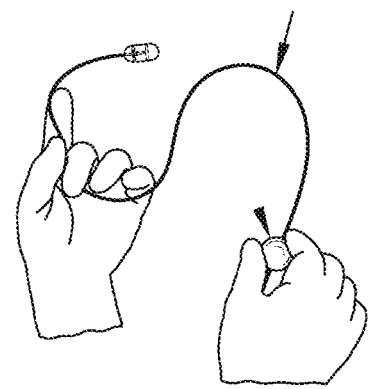
Figure 11A:
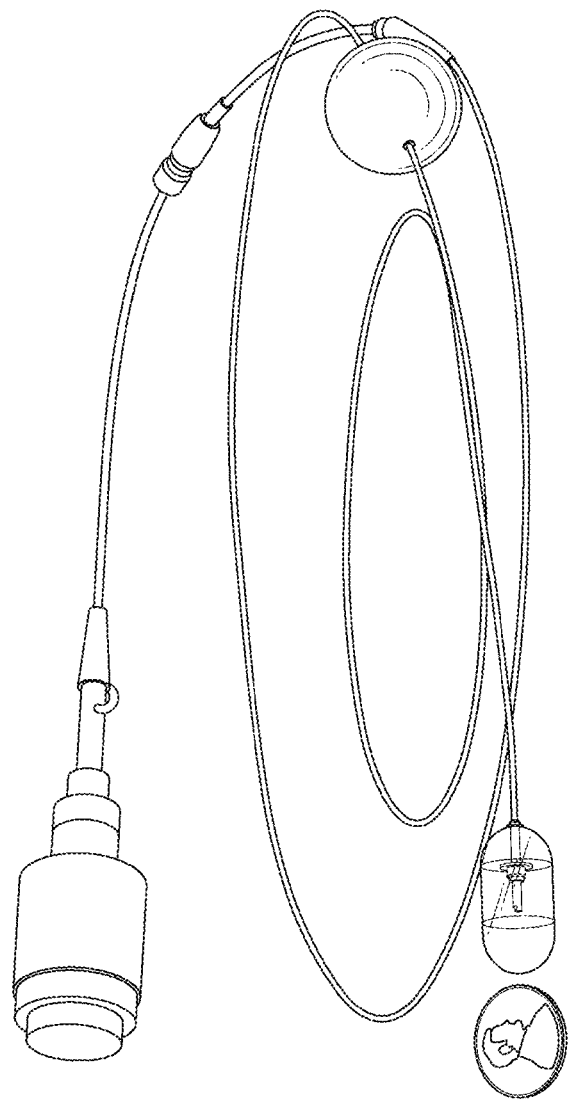
Figure 11D:
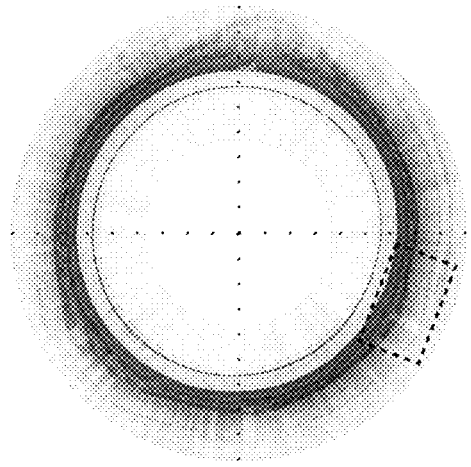
Figure 11E:
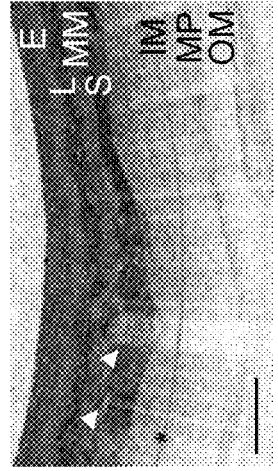
Figure 11F:
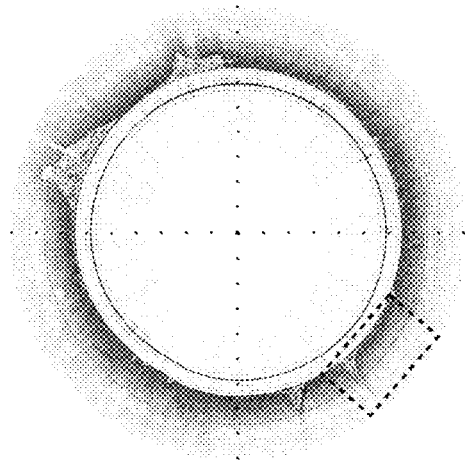
Figure 11G:
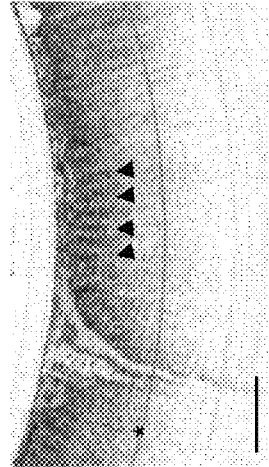
Figure 11H:
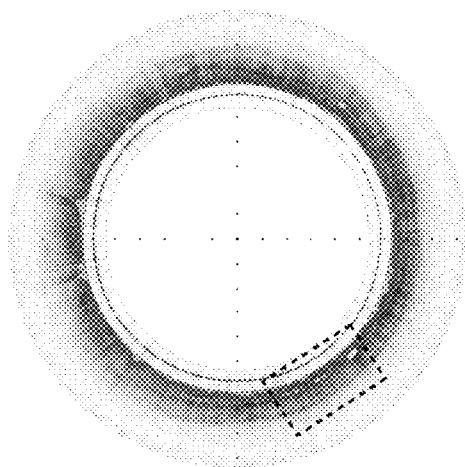
Figure 11I:
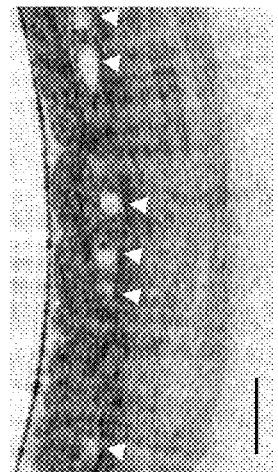

FIG. 6 shows a schematic cross-sectional view of an exemplary optical system for focusing light beam at the tissue in the luminal organs imaging system according to an exemplary embodiment of the present disclosure. This exemplary embodiment can be used in and/or all exemplary embodiments of the capsule catheter described herein. In the exemplary embodiment shown in FIG. 6, a GRIN lens 650 can be used for focusing light at the working distance defined by capsule diameter. Placing an optical fiber 600 in a ferrule 630 can assist with centration and angle polishing of a tip of the fiber 600. The polished ferrule 630, together with the fiber 600, can be assembled with a spacer 640. A light beam 155 (or other electro-magnetic radiation) can expand over the length of the spacer 640, and then focused by the GRIN lens 650 or similar optical element or arrangement. A right angle prism 660 can direct the light beam (or other electro-magnetic radiation) 155 to the side of the optical probe. The prism 660 can be coated with aluminum and/or other material on hypotenuse, e.g., to improve reflection efficiency, and with antireflective coating at the outside facing leg to decrease light backreflection. By changing the length of the spacer 640 and the GRIN lens 650, different optical properties of the light beam 155, e.g., working distance and spot size at the focus, can be achieved. The optics arrangement can be protected by an outer tube 215, and the fiber 600 can be protected by an outer tube 610, which can be a driveshaft enabling rotating of the optical assembly. The exemplary optical system of FIG. 6 can be included in the capsule catheter with the spinning inner optical core, as shown in FIG. 9.

Figure 7B:
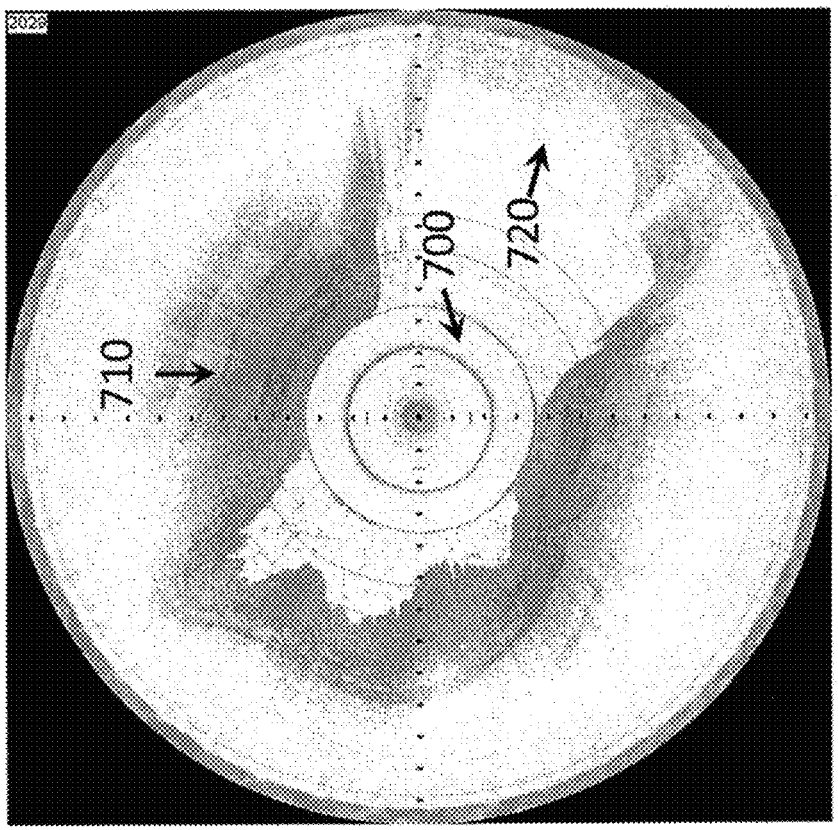
FIG. 7B is an exemplary circumferential OFDI frame representing a cross-section from the human esophagus in a partial contact with the capsule.
Figure 7A:
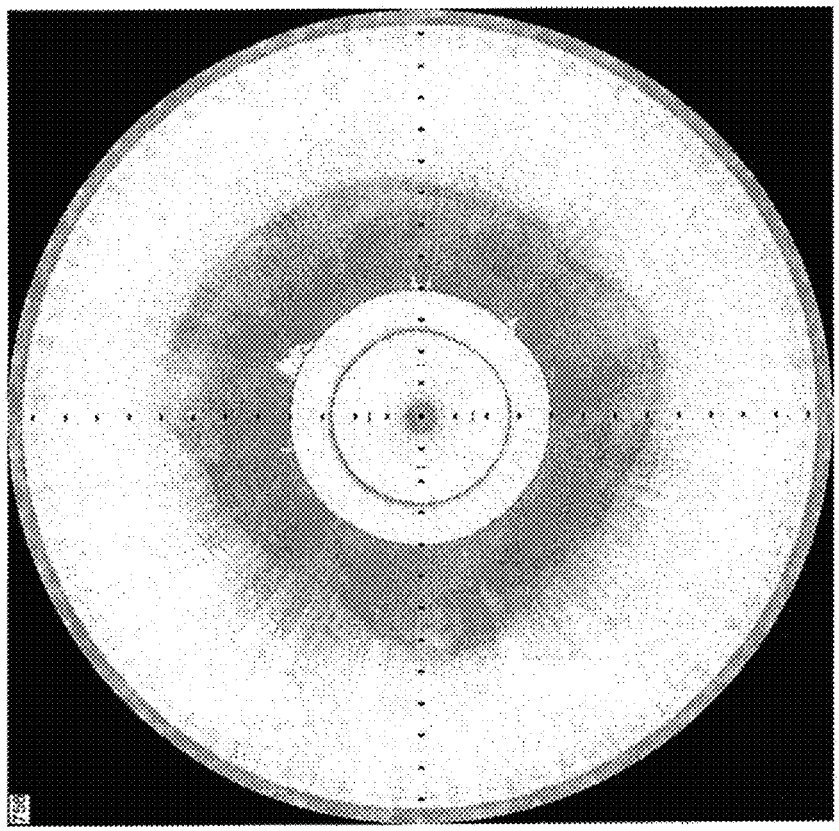
FIG. 7A is an exemplary circumferential OFDI frame representing a cross-section from a human esophagus in full contact with the capsule.

FIGS. 7A and 7B illustrate exemplary circumferential OFDI frames from human esophagus obtained using an exemplary embodiment of the apparatus, device and method according to the present disclosure. For example, the exemplary images shown in FIG. 7A and FIG. 7B were acquired in the same subject in different locations in the esophagus. For example, due to the peristalsis, the capsule wall 700 can be either in full contact with tissue 710 (as shown in FIG. 7A) or in a partial contact 720 (as shown in FIG. 7B). In the area with a partial contact 720, the tissue can be out of the imaging range of the OFDI system. Thus, one of the preferences for the exemplary imaging system used for this application can be an extended imaging range. In this exemplary case, the imaging range equals about 6.4 mm in air. Doubling this range or implementing an automatic ranging mechanism to adjust raging depth can be used. An additional embodiment includes a capability to extend the axial focus of the imaging beam for cases when the tissue is not in precise contact with the capsule. These axial focusing extending arrangement(s) can include binary or phase apodization, axicon lenses, and Bessel beam generating means.

In order to properly reconstruct volumetric dataset, information about current position of the capsule and its speed during pullback can be used. In one exemplary embodiment, such information can be achieved by constant pulling of the capsule, and recording its position by reading distance marks at the tether. In another exemplary embodiment, the marks can be recorded by encoder mounted on a reference point, for instance the bite protection and the distance can be automatically acquired. In other embodiment a transmitter can be implemented into the capsule body and the receiver placed outside of the subject can read its position. In still another exemplary embodiment, the capsule includes a pressure sensor that can provide information about pressure in the anatomical structure that is related to its position.

Referring now to FIG. 8, in yet another embodiment of this invention, the tether of the capsule 800 is removed in its entirety and the capsule is configured to acquire microscopic images from the tissue structure of interest. The microscopic imaging modality can be one or more of optical frequency domain imaging, optical coherence tomography, SD-OCT, confocal microscopy, spectrally-encoded confocal microscopy, two photon microscope, second harmonic microscopy, third harmonic microscope, CARS, stimulated Raman microscopy, etc. A light source 805 can be or include a laser, LED, SLD, tunable laser, pulsed laser or other such light source. A detector 815 can be or include a single detector, linear array detector, or area array detector, such as a CCD or CMOS chip. In yet another exemplary embodiment, the optics 830 can be moved by an actuation or beam scanning arrangement(s), such as a motor 840 and/or linear actuator. The image data can be obtained from the detector 815, and processed by a computer processing arrangement 825. Microscopic information from the sample can be transmitted externally to the tissue and in one embodiment outside the body using an element that transmits a portion of the electromagnetic radiation including but not limited to RF electromagnetic radiation via an antenna 810, and it is also possible to include a light transmitting arrangement, especially if the light is in a NIR window (e.g., about 600-2000 nm), where an external detector can receive the image encoded on a light signal that is transmitted through the body.

In yet another exemplary embodiment, the image information can be stored on solid state storage inside the capsule that is read out after the capsule has been retrieved. In a further exemplary embodiment, the microscopic capsule can be configured to have an arrangement for a self-propulsion that can be controlled internally and/or externally, including but not limited to propellers, arms emanating from the capsule or other propulsion arrangement(s). According to exemplary embodiment according to the present disclosure, a battery or series of batteries 820 can be include that can provide power to at least one of the electronics, light source, detector apparatus, and motion transduction, locomotion, RF and light transmitter elements. In yet further exemplary embodiments, the position of the microscopic imaging capsule can be controlled by an external magnetic field and/or the power can be supplied by an oscillating magnetic field. In still another exemplary embodiment, the microscopic capsule can contain a video camera for acquiring video images, in addition to the microscopic image data. In yet a further exemplary embodiment, the capsule can contain a balloon that can be inflated once it reaches a predetermined portion of the anatomical structure. In a further exemplary embodiment, the capsule can contain a position sensing mechanism that provides information, which is also transmitted externally to the body or saved via an internal storage arrangement.

Exemplary embodiments of the present disclosure can provide further uses for medical screening and diagnosis of the GI tract organs. The brevity and ease with which the exemplary procedures according to the present disclosure can be performed can facilitate an internal microscopic imaging in virtually any health care setting, including in the primary care physician's office. In addition, because the exemplary embodiments of the devices according to the present disclosure can be retrieved and sterilized, capsule endomicroscopy can be inexpensive, making it feasible to screen large populations for upper digestive diseases. It is also possible to implement tether-free pills that can be battery-powered and incorporate wireless technology, including, e.g., RF transmitters, the addition of other in vivo microscopy technologies, such as, e.g., confocal microscopy and/or the incorporation of locomotion, biopsy, and concomitant therapy functionalities. Addition of other imaging modalities to the exemplary capsule can also further increase its utility, including, but not limited to fluorescence imaging and microscope, Raman spectroscopy, Reflectance spectroscopy, and conventional white light imaging.

While the exemplary embodiments of the present disclosure have been described herein with reference to the use thereof in the upper GI tract, e.g., the esophagus, it should be clear that every one of the exemplary embodiments described herein can also be utilized in other areas of the GI tract and other portions of a subject, including the small bowel and colon. In one example, the tether can be made of sufficient length to enable the transit of the capsule therein. Indeed, the exemplary embodiments of the present disclosure can be used with and for other luminal organs of the body, including but not limited to bladder, uterus, pulmonary airways, gallbladder, larynx, and other ductal and luminal anatomical structures. Furthermore, potential spaces of the body can also be utilized, including but not limited to the abdominal and peritoneal cavities.

According to yet another exemplary embodiment of the present disclosure, an exemplary configuration of a common-path capsule can be provided that may be used when an interferometry is utilized to obtain information regarding luminal organ. Such exemplary capsules are shown in FIGS. 10A and 10B. In such exemplary embodiments shown in FIGS. 10A and 10B, a reference arm and a sample arm are combined in one optical path within the capsule catheter. This exemplary configuration can simplify the exemplary imaging system by solving problem of dispersion and polarization imbalance between the arms. A reference signal can be generated by reflecting small portion of light (or other radiation) from additional partially reflecting surface in front of the tissue (or portion(s) thereof). The remainder of the light/radiation 155 (e.g., sample arm light) can be focused into the tissue, e.g., at a location that is outside of the capsule's outer wall. In the exemplary embodiment shown in FIG. 10A, the reference signal can be back-reflected from the semi reflective surface 1020 mounted in the optical probe-housing 1010, which can position the surface 1020 in the optical path of the light 155. Two-dimensional imaging can be obtained by rotating of the mount 1010, which can comprise an optical probe and a reflective surface 1020. The mount 1010 can additionally center the optical probe within the capsule during spinning, and can be made from, at least in part, nylon or other material providing minimal friction with the capsule wall. In yet another embodiment shown in FIG. 10B, the reference signal can be obtained by placing a reflective ring 1030 in the capsule wall. Such ring 1030 can be obtained by coating of the capsule wall and/or adding an element, which will be positioned in the optical path of the light/radiation 155.

Figure 13:
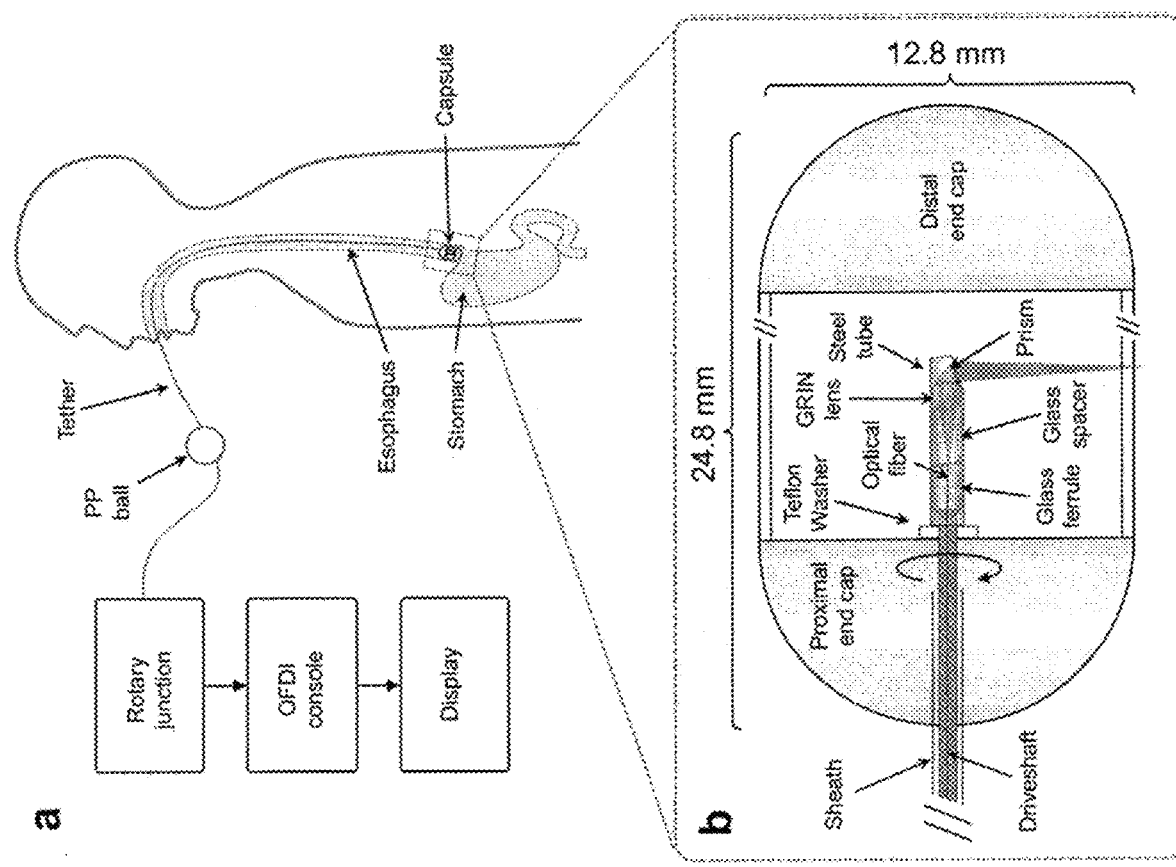
FIG. 13, panel (b) is an expanded schematic of a capsule provided in the tethered capsule endomicroscopy device shown in FIG. 13, panel (a).

According to still exemplary embodiment of the present disclosure, a tethered optomechanical capsule device, as shown in FIG. 11, panels (a)-(c), FIG. 13, panels (a) and (b) can be provided that can captures three-dimensional microscopic images of the digestive organs after it has been swallowed. The tethered capsule device can employ optical frequency domain (OFDI) imaging technology (see, e.g., Yun, S. H., et al., Nat Med, Vol. 12, pp. 1429; 1433, 2006) to provide cross-sectional architectural morphologic data that has previously been shown to facilitate a diagnosis of Barrett's and high-grade neoplastic changes in the esophagus. (See Evans, J. A. et al., Gastrointest Endosc, Vol. 65, pp. 50-56, 2007; Evans, J. A. et al., Clin Gastroenterol Hepatol, Vol. 4, pp. 38-43, 2006; and 8. Poneros, J. M., et al., Gastroenterology, Vol. 120, pp. 7-12, 2001).

For example, a capsule portion of the exemplary device can be connected to a thin, string-like tether that can facilitate the operator to control the position of the capsule in the gastro-intestinal (GI) tract, thereby effectuating a circumferential scan of the miniature focusing optics in the capsule, and transceiving light or other electro-magnetic radiation to and/or from the capsule. When swallowed, the luminal organs can constrict around the capsule and gradually pushing it down the GI tract under the natural propulsion force of peristalsis. Once the capsule reaches the distal-most region of interest, it can be pulled back using the tether, again while imaging.

Figure 12:
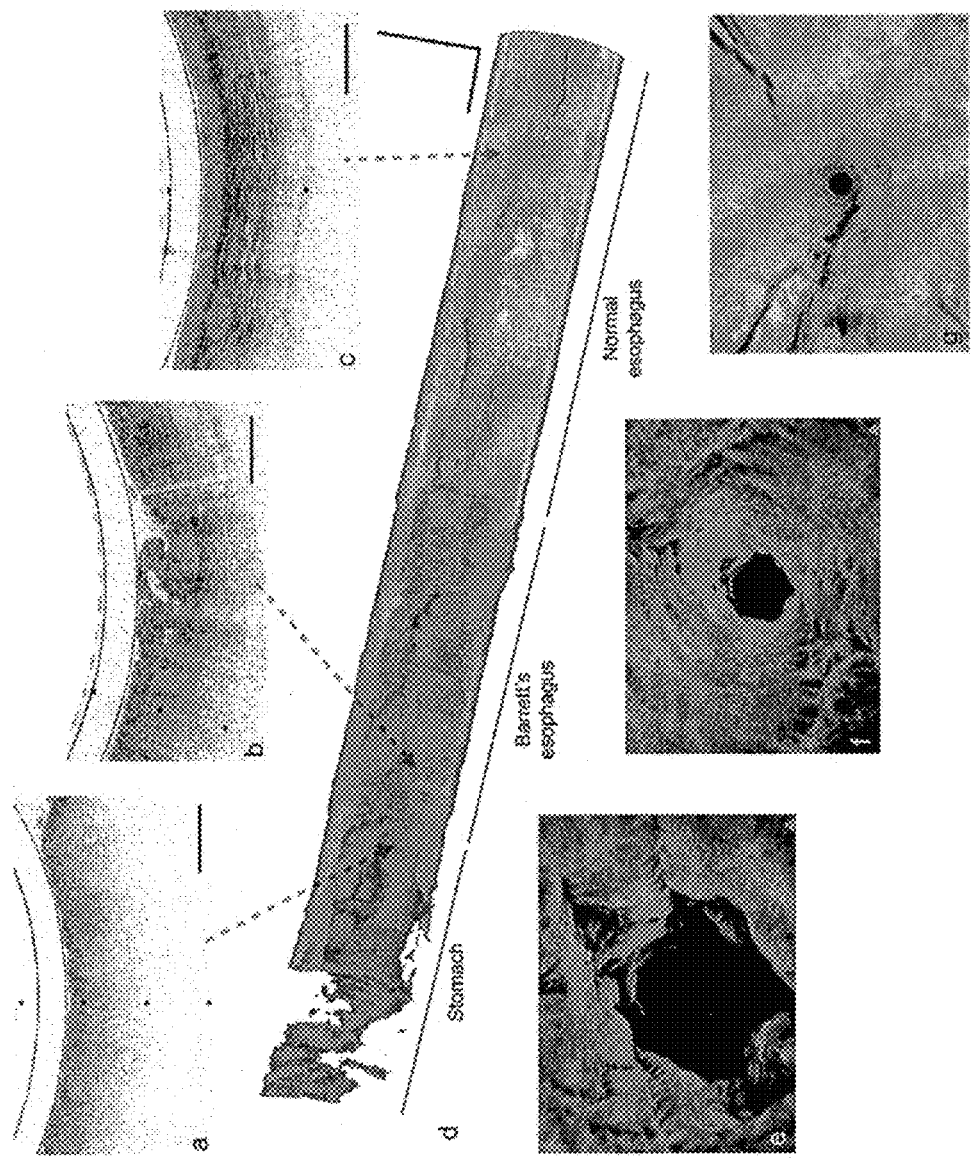
FIG. 12, panel (a) is a portion of a cross-sectional tethered capsule microscopy image of stomach from a patient with a diagnosis of Barrett's esophagus and high-grade dysplasia/intramucosal carcinoma that can be seen at the distal end of the esophagus, which utilizes the exemplary tethered capsule endomicroscope device shown in FIG. 11, panel (a)

According to one exemplary embodiment of the present disclosure, during the transit of the exemplary capsule, e.g., multiple 30 μm (lateral)×7 μm (axial) resolution OFDI cross-sections of the luminal organ (as shown in FIG. 11, panels (d), (f) and (h)) can be acquired facilitating a visualization of normal squamous mucosa (see FIG. 11, panel (e) and FIG. 12, panel (c)), stomach (see FIG. 11, panel (g) and FIG. 12, panel (a)), and Barrett's epithelia (see FIG. 11, panel (i) and FIG. 12, panel (b)). Sequential cross-sections may also be compiled to reconstruct a three-dimensional microscopic representation of the entire luminal organ (see FIG. 12, panels (d)-(g)). After the exemplary procedure is completed, the exemplary capsule can be withdrawn through the mouth, and disinfected for reuse.

In an exemplary study of 13 subjects (normal volunteers (n=7), volunteers with known Barrett's esophagus (n=6)), it was determined that using the exemplary device according to the exemplary embodiment of the present disclosure shown in FIG. 11, panels (a), (b) and (c), the mean transit time for imaging ~15 cm length of esophagus was only about 58 sec. When implementing, e.g., four imaging passes (two up and two down), resulting in four complete datasets, the entire procedure lasted an average of approximately 6 minutes (6 min 18 sec) from the capsule insertion to its extraction. There were no visible complications of tethered capsule endomicroscopy noticed. Following the exemplary procedure, the majority (12/13) of the subjects reported that they would prefer tethered capsule endomicroscopy to conventional endoscopy.

Tethered capsule endomicroscopy procedures and devices can provide advantageous possibilities for medical screening and diagnosis of GI tract organs. Because these images are obtained from singly scattered light rather than the multiply scattered color reflectance of endoscopy, such images can provide architectural microscopic image information that can be spatially correlated with histopathology from corresponding locations. (See Evans, J. A., et al. Gastrointest Endosc, Vol. 65, pp. 50-56, 2007; Evans, J. A., et al., Clin Gastroenterol Hepatol, Vol. 4, pp. 38-43, 2006; and 8. Poneros, J. M., et al., Gastroenterology, Vol. 120, pp. 7-12, 2001). The exemplary device according to an exemplary embodiment of the present disclosure, can acquire, three-dimensional microscopic image data from large segments of luminal tissues, thus facilitating a comprehensive assessment of subsurface microstructures that are not evident and can be missed by endoscopy.

Since the exemplary embodiment of tethered endomicroscopy capsule device according to the present disclosure can traverse the GI tract without visual guidance, the training required to conduct the procedure is minimal. Such exemplary benefits and the brevity and ease with which the exemplary procedure can be performed can facilitate the performance of internal microscopic imaging in many health care settings, including in the primary care physician's office. In addition, because the exemplary embodiment of tethered endomicroscopy capsule device according to the present disclosure can be retrieved and disinfected, tethered capsule endomicroscopy would likely be inexpensive (see Ramirez, F. C. et al., Gastrointest Endosc, Vol. 61, pp. 741-746, 2005), thus making it feasible to screen large populations for upper digestive diseases.

It was also determined that the degree to which the esophagus remained close to the outer surface of the pill in a manner such that high quality images were obtained (an average of 94.5% of all frames) using the exemplary device according to the present disclosure. Such exemplary result can indicate that other in vivo endomicroscopy technologies, such as confocal microscopy, (see can also be effective when implemented using a capsule. In addition, it is possible to implement tether-free pills, as well as provide the addition of video imaging for guidance and the incorporation of externally-controlled locomotion and concomitant biopsy and therapy functionalities. (See Quirini, M. et al., Gastrointest Endosc, Vol. 67, pp. 1153-1158, 2008; Kim, B. et al., Sensors and Actuators A: Physical, Vol. 125, pp. 429-437, 2006; and Vakoc et al., Biomed Opt, Vol. 12, 020501, 2007).

Exemplary Procedures
Exemplary Use of OFDI Technology

OFDI is a cross-sectional, interferometric microscopic imaging technique that records light reflected as a function of depth within tissue (see Yun, S. et al., Opt Express, Vol. 11, pp. 2953-2963, 2003), information that may be used to accurately render pathologic diagnoses in digestive tract tissues such as the esophagus (see Evans, J. A., et al., Gastrointest Endosc, Vol. 65, pp. 50-56, 2007). The exemplary OFDI system according to the exemplary embodiment of the present disclosure as shown in FIG. 13, panels (a) and (b) can illuminated tissue using, e.g., near-infrared (NIR) wavelengths sweeping from about 1250 nm to 1380 nm. Exemplary circumferential, cross-sectional images can be acquired at, e.g., 20 frames second$^{-1}$ using, e.g., a total of 2048 axial (depth) scans per image. Axial resolution can be, e.g., 7 µm in tissue (estimated refractive index n=1.4) and the sensitivity can be ~110 dB. It should be understood that various wavelengths, numbers of axial scans can be used, resolutions and sensitivities can be achieved and/or used that are within the scope of the present disclosure.

During the exemplary procedure, as one example, all raw data in real time can be recorded and also displayed subsampled versions of the images in real time. Immediately following the imaging session, e.g., it is possible to reconstruct the images at full resolution (e.g., about 2900×2900 pixels) and display them using, e.g., an inverse gray scale lookup table. It is possible, according to one exemplary embodiment, to automatically align frames and rotationally registered them using, e.g., cross-correlation in ImageJ. It is possible to remove signals from the capsule's inner and outer surfaces prior to three-dimensional volume rendering (Osirix 4.0). An exemplary percentage of frames can be measured, where the capsule can be in proximity to the esophagus by dividing the number of frames in which the esophageal wall was clearly visible for greater than, e.g., 50% of its circumference by the total number of frames.

Exemplary Tethered Capsule Endomicroscope Device

As shown in FIG. 13, panel (a), the exemplary capsule can be attached to a tether. A polypropylene (PP) ball handle can be affixed to the tether, which can be, e.g., about 60 cm from the exemplary capsule. The tether can terminate at the rotary junction, which can be connected to the imaging console and display. Together, the ball and tether can facilitate control of the capsule's location and provide a way for extracting the exemplary capsule from the subject when the procedure is complete.

The exemplary capsule according to an exemplary embodiment of the present disclosure can also comprise, e.g., a 12.8 mm (diameter)×24.8 mm (length) transparent, cylindrical shell bounded by hemispherical end caps (as shown in FIG. 13, panel (b)). According to one exemplary embodiment, the shell can enclose miniature optics that can redirect focused (FWHM diameter of about 30 µm) light or other radiation outside the exemplary capsule. The capsule can be connected to a flexible (e.g., 0.96 mm diameter) sheath, which can serves as a tether. The sheath can enclose a driveshaft and an optical fiber; and the fiber can transmit light or other radiation to and receives light (or other radiation) from the miniature optics inside the capsule. The driveshaft can convey a rotational torque from the system's optical rotary junction to the capsule's optics. Circumferential, cross-sectional images can be acquired as the rotary junction, and thus the optical beam in the capsule continuously spins.

As shown in FIG. 13, panel (b), within the capsule, the driveshaft can be connected to a steel tube that contains the miniature imaging optics, including, e.g., a ferrule, spacer, GRIN lens, and 45-degree reflecting prism. Proximal rotational motion of the driveshaft and fiber at the rotary junction is transduced to the distal steel tube and optics in the capsule, causing the focused beam 1 to rotate around the outer circumference of the capsule. The Teflon washer acts as a bearing to reduce friction between the steel tube and the proximal end cap.

Three-dimensional images can be obtained while acquiring cross-sectional images as the tethered capsule moves up and down the digestive tract.

Exemplary Imaging Procedure

Subjects were asked to swallow the exemplary capsule endomicroscope, and then take a sip of water. While the operator held the tether, the capsule was gently allowed to descend through the esophagus to the stomach. The distance between the capsule and the incisors was recorded using 5-cm-spaced marks on the tether. Exemplary images were visualized in real time to determine when the capsule had reached the stomach. Once in the stomach, the pill up was gradually pulled back through the esophagus to the mouth while imaging. For example, four imaging passes have been performed (two up and two down) in each subject. Following imaging, the tethered capsule was removed and disinfected it for reuse in accordance with the standard procedure for the disinfection of GI endoscopes (e.g., submersion in Cidex OPA for 12 minutes).

The foregoing merely illustrates the principles of the disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems, and for example with those described in International Patent Application No. PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Application Publication No. 2006/0093276 on May 4, 2006, and U.S. patent application Ser. No. 10/501,276, filed Jul. 9, 2004 which published as U.S. Patent Application Publication No. 2005/0018201 on Jan. 27, 2005, and U.S. Patent Application Publication No. 2002/0122246, published on May 9, 2002, the disclosures of which are incorporated by reference herein in their entireties. It will thus be appreciated that those skilled in the art will be able to devise numerous systems, arrangements and methods which, although not explicitly shown or described herein, embody the principles of the disclosure and are thus within the spirit and scope of the present disclosure. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly incorporated herein in its entirety. All publications referenced herein can be incorporated herein by reference in their entireties.

What is claimed is:

1. An apparatus for obtaining data for at least one portion within at least one luminal or hollow sample, comprising:

a first optical arrangement comprising an optical core configured to transceive at least one electromagnetic radiation to and from the at least one portion;

a wavelength dispersive second arrangement comprising a diffraction grating which is configured to disperse the at least one electromagnetic radiation and configured to rotate about an axis that is substantially parallel to a central axis of a housing, wherein the at least one electromagnetic radiation comprises electromagnetic radiation having a plurality of different wavelengths, and wherein the diffraction grating is configured to disperse the plurality of different wavelengths along different spatial locations of the at least one portion; and the housing comprising a rigid capsule, and enclosing the first and second arrangements;

an optical fiber drive shaft coupled to a rotational mechanical arrangement, and wherein the optical fiber drive shaft is coupled to the wavelength dispersive second arrangement such that rotation of the optical fiber drive shaft causes the wavelength dispersive second arrangement to rotate about an axis that is substantially parallel to a central axis of the housing.

2. The apparatus according to claim 1, further comprising a tether arrangement connected to a proximal end of the housing.

3. The apparatus according to claim 2, further comprising a further arrangement configured to track at least one of position, acceleration or velocity of the tether.

4. The apparatus according to claim 1, further comprising a further arrangement configured to track at least one of position, acceleration or velocity of the apparatus.

5. The apparatus according to claim 1, further comprising a video camera arrangement which is coupled to the housing.

6. The apparatus according to claim 1, wherein the different spatial locations differ along a dimension that is substantially parallel to a surface of the at least one portion.

7. The apparatus according to claim 2, wherein the tether arrangement contains the optical fiber drive shaft coupled to the rotational mechanical arrangement.

8. The apparatus according to claim 1, further comprising an imaging arrangement which generates an image of the at least one portion when the wavelength dispersive second arrangement is rotated and causes the at least one electromagnetic radiation to radiate with a particular radiation pattern on the at least one portion.

9. The apparatus according to claim 1, further comprising:
a light source arrangement optically coupled to the wavelength dispersive second arrangement via the first optical arrangement, wherein the light source arrangement is configured to emit the at least one electromagnetic radiation toward the wavelength dispersive second arrangement;
a battery arrangement which provides energy to the light source arrangement;
a radio frequency transmitter arrangement coupled to the battery arrangement; and
a data storage arrangement coupled to the battery arrangement and the radio frequency transmitter arrangement.

10. The apparatus according to claim 9, further comprising:
a motor arrangement coupled to the battery arrangement and the wavelength dispersive second arrangement,
wherein the motor arrangement is configured to cause the wavelength dispersive second arrangement to rotate about an axis that is substantially parallel to a central axis of the housing.

11. The apparatus according to claim 10, further comprising:
a detector arrangement that is optically coupled to the wavelength dispersive second arrangement via the first optical arrangement,
wherein the detector arrangement is configured electromagnetic radiation returned from the at least one portion; and
a processor arrangement electrically coupled to the battery arrangement, the motor arrangement, the radio frequency transmitter arrangement, the data storage arrangement, and the detector arrangement,
wherein the processor arrangement is programmed to:
cause the motor arrangement to rotate the wavelength dispersive second arrangement while the light source arrangement emits the at least one electromagnetic radiation toward the wavelength dispersive second arrangement;
cause the detector arrangement to generate image data based on the electromagnetic radiation returned from the at least one portion;
cause the image data to be recorded using the data storage arrangement; and
cause data representative of the image data to be transmitted using the radio frequency transmitter arrangement.

12. An apparatus for obtaining data for at least one portion within at least one luminal or hollow sample, comprising:
an optical first arrangement configured to transceive at least one electromagnetic radiation to and from the at least one portion
wherein the at least one electromagnetic radiation comprises electromagnetic radiation having a plurality of different wavelengths,
a diffractive optical element comprising a diffraction grating configured to rotate about an axis that is substantially parallel to a central axis of a housing,
wherein the diffraction grating is configured to disperse the plurality of different wavelengths along different spatial locations of the at least one portion;
a second arrangement which is configured to forward at least one return radiation from the at least one luminal or hollow sample to an optical microscopy system, wherein at least one portion of an outer periphery of the apparatus has a shape of a pill; and
a third arrangement which includes at least one of (i) a battery arrangement which provides energy to the optical microscopy system, (ii) a radio frequency transmitter arrangement, (ii) a light source arrangement, or (iv) a data storage arrangement;
an optical fiber drive shaft coupled to a rotational mechanical arrangement,
wherein the optical fiber drive shaft is coupled to the wavelength dispersive second arrangement such that rotation of the optical fiber drive shaft causes the wavelength dispersive second arrangement to rotate about an axis that is substantially parallel to a central axis of the housing.

13. The apparatus according to claim 12, further comprising a propulsion arrangement which moves the apparatus within the at least one luminal or hollow sample.

14. An apparatus for obtaining data for at least one portion within at least one luminal or hollow sample, comprising:

a first optical arrangement configured to transceive at least one electromagnetic radiation to and from the at least one portion;
a wavelength dispersive second arrangement comprising a diffraction grating which is configured to disperse the at least one electromagnetic radiation and configured to rotate about an axis that is substantially parallel to a central axis of a housing,
   wherein the at least one electromagnetic radiation comprises electromagnetic radiation having a plurality of different wavelengths,
   wherein the diffraction grating is configured to disperse the plurality of different wavelengths along different spatial locations of the at least one portion:
   wherein the housing includes a rigid capsule enclosing the first and second arrangements;
a tether arrangement connected to a proximal end of the housing and containing an optical fiber drive shaft coupled to a rotational mechanical arrangement,
   wherein the optical fiber drive shaft is coupled to the wavelength dispersive second arrangement such that rotation of the optical fiber drive shaft causes the wavelength dispersive second arrangement to rotate about an axis that is substantially parallel to a central axis of the housing.

15. An apparatus, comprising:
a housing comprising a rigid capsule;
a diffractive optical element comprising a diffraction grating rotatably coupled to the housing and configured to rotate about an axis that is substantially parallel to a central axis of the housing;
a first transmissive optical element that is mechanically coupled to the housing and optically coupled to the diffractive optical element,
   the first transmissive optical element having a proximal end and a distal end, and
   the first transmissive optical element being configured to:
      receive light at the proximal end,
      emit the received light from the distal end toward the diffractive optical element,
         wherein the diffractive optical element is rotated by a motor while the light is emitted from the distal end of the first transmissive optical element towards the diffractive optical element,
      wherein the light emitted from the distal end of the first transmissive optical element comprises a plurality of different wavelengths of light, and
      wherein the diffraction grating is configured to disperse the plurality of different wavelengths toward different portions of a sample, receive reflected light that has been reflected by the sample at the distal end, and
      emit the reflected light toward a second transmissive optical element that is configured to be optically coupled to a detector.

16. The apparatus of claim 15, wherein the first transmissive optical element comprises a gradient index (GRIN) lens, and
   wherein the second transmissive optical element is an optical fiber coupled to a proximal end of the housing.

17. The apparatus of claim 16, further comprising:
a tether coupled to the proximal end of the housing;
a driveshaft disposed within the tether,
   wherein a proximal end of the driveshaft is configured to be coupled to a rotary junction,
   wherein a distal end of the driveshaft is mechanically coupled to the first transmissive optical element, and
   wherein a majority of the optical fiber is disposed within the driveshaft.

18. The apparatus of claim 15, wherein the first transmissive optical element comprises an optical circulator configured to:
   emit light received at the proximal end from the distal end, and
   emit light received at the distal end from a third port that is optically coupled to the detector.

19. The apparatus of claim 15, wherein the diffractive optical element is mechanically coupled to the motor, wherein the motor is disposed within the housing.

20. The apparatus of claim 15, wherein the different portions differ along a dimension that is substantially parallel to a surface of the sample.

21. The apparatus of claim 15, wherein the diffractive optical element is mechanically coupled to the second transmissive optical element.

22. The apparatus of claim 15, wherein the apparatus is configured to be operatively coupled to a spectrally encoded confocal microscopy (SECM) imaging system, and
   wherein the apparatus is used to generate SECM image data.

* * * * *